(12) United States Patent
Oster et al.

(10) Patent No.: US 8,884,045 B2
(45) Date of Patent: Nov. 11, 2014

(54) USE OF AN ACETIC ACID WASH TO PREPARE LOW-SULFATE 5-SULFOISOPHTHALIC ACID, MONO-LITHIUM SALT

(75) Inventors: Timothy A. Oster, Batesville, AR (US); Michael Todd Coleman, Batesville, AR (US)

(73) Assignee: Future Fuel Chemical Company, Clayton, MO (US)

( * ) Notice: Subject to any disclaimer, the term of this patent is extended or adjusted under 35 U.S.C. 154(b) by 0 days.

(21) Appl. No.: 13/880,602

(22) PCT Filed: Mar. 29, 2011

(86) PCT No.: PCT/US2011/030252
§ 371 (c)(1),
(2), (4) Date: Apr. 19, 2013

(87) PCT Pub. No.: WO2012/054097
PCT Pub. Date: Apr. 26, 2012

(65) Prior Publication Data
US 2013/0211120 A1    Aug. 15, 2013

Related U.S. Application Data

(63) Continuation-in-part of application No. PCT/US2010/053186, filed on Oct. 19, 2010.

(51) Int. Cl.
*C07C 303/44* (2006.01)
*C07C 309/77* (2006.01)
*C07C 303/32* (2006.01)

(52) U.S. Cl.
CPC ............. *C07C 303/44* (2013.01); *C07C 303/32* (2013.01); *C07C 309/77* (2013.01)
USPC ............................................................ 558/53

(58) Field of Classification Search
CPC .. C07C 309/58; C07C 303/32; C07C 303/44; C07C 303/22; C07C 309/77
USPC ............................................................. 558/53
See application file for complete search history.

(56) References Cited

U.S. PATENT DOCUMENTS 4,303,577 A    12/1981   Ridgway et al.
H1760 H   *  11/1998   Elango et al. ................... 560/14

(Continued)

FOREIGN PATENT DOCUMENTS

CN     1203909 A    1/1999
CN     1673450 A    9/2005

(Continued)

OTHER PUBLICATIONS

US Statutory Invention Registration H1760 (Elango, Waradaraj et al.) Nov. 3, 1998.

(Continued)

*Primary Examiner* — Kristin Vajda
*Assistant Examiner* — Valerie Rodriguez-Garcia
(74) *Attorney, Agent, or Firm* — Husch Blackwell LLP

(57) ABSTRACT

There is disclosed a process for making a mono-lithium salt of 5-sulfoisophthalic acid (LiSIPA) having less than 500 ppm sulfate. The process uses a reaction mixture of water, a lithium cation producing compound, and 5-sulfoisophthalic acid. The reaction mixture is heated to reflux, cooled, filtered and washed with acetic acid to obtain a high quality LiSIPA having less than 500 ppm sulfate. Also disclosed is a high quality, non-purified reaction product containing a mono-lithium salt of 5-sulfoisophthalic acid and having less than 500 ppm sulfate.

16 Claims, 1 Drawing Sheet

(56) References Cited

U.S. PATENT DOCUMENTS

| | | | |
|---|---|---|---|
| 6,133,382 | A | 10/2000 | Studholme |
| 6,334,877 | B1 * | 1/2002 | Studholme .................. 8/115.56 |
| 6,355,835 | B1 | 3/2002 | Kulsrestha et al. |
| 6,479,619 | B1 | 11/2002 | Duan |
| 6,706,852 | B2 | 3/2004 | Duan et al. |
| 8,297,035 | B2 | 10/2012 | Chikatsune et al. |
| 2002/0169273 | A1 * | 11/2002 | Duan ........................... 528/286 |
| 2004/0242838 | A1 | 12/2004 | Duan |
| 2007/0088133 | A1 | 4/2007 | Heater |
| 2007/0208200 | A1 | 9/2007 | Parker et al. |

FOREIGN PATENT DOCUMENTS

| | | | |
|---|---|---|---|
| CN | 200610043229 | | 8/2006 |
| CN | 101279940 | | 10/2008 |
| CN | 101279940 | A | 10/2008 |
| CS | 119642 | | 8/1966 |
| CS | 157260 | | 4/1975 |
| DE | 1938227 | A | 2/1971 |
| IN | 172789 | A1 | 11/1993 |
| JP | 48080539 | A | 10/1973 |
| JP | 51004142 | A | 1/1976 |
| JP | 04247064 | | 9/1992 |
| JP | 2004331527 | A | 11/2004 |
| JP | 2005145836 | A | 6/2005 |
| WO | 2009072144 | A2 | 6/2009 |
| WO | 2011049940 | A2 | 4/2011 |

OTHER PUBLICATIONS http://www.xuyechem.com/pages/lisipa.htm (Jun. 15, 2008).

Yu, et al., Synthesis of sodium bis(2-hydroxyethyl) 5-sulfoisophthalate, Huaxue Shijie, 2005, pp. 26-29, vol. 46 Issue 1, China.

Zhao, et al., Synthesis of medium-temperature SIPE, Hecheng Xianwei Gongye, 2001 pp. 5-9, vol. 24, Issue 6, China.

Tang, et al. Improvement on the synthetic process of dimethyl 5-sulfolsophthalate sodium salt, Qingdao Keji Daxue Xuebao, Ziran Kexueban 2003, pp. 113-116, vol. 24, Issue 2, China.

Zhang, et al., New process for the manufacture of dimethyl 5-sulfosophthalate sodium salt, Jingxi Huagong, 2000, pp. 633-636, vol. 17, Issue 11, China.

Zhang, Production technique for dimethyl sodiosulfolsophthalate, Juzhi Gongye Bianjibu, 2002, pp. 20-22, vol. 15, Issue 1, China.

Wu, et al., Study on the production of dyeing modifier SIPM for polyester fiber, Hecheng Xianwei Gongye, 1995, pp. 11-13, vol. 18, Issue 2, China.

Wu, et al., Synthesis of dyeing improver for cationic dye dyeable polyester fibers, Dalian Ligong Daxue Xuebao, 1995, pp. 434-436, vol. 35, Issue 3, China.

Jiang, et al., Synthesis of sodium 3,5-dimethoxycarbonyl benzene sulfonate, Huagong Shikan, 2000, pp. 21-23, vol. 14, Issue 5, China.

Zhang, et al., Synthesis of sodium 5-sulfodimethylisophthalate, Jingxi Huagong Bianjibu, 1998, pp. 39-41, vol. 15, Issue 3, China.

Li, et al., Synthesis of sodium dimethyl 5-sulfoisophthalate, Jingxi Huagong Bianjibu, 2003, pp. 50-52, vol. 20, Issue 1, China.

* cited by examiner

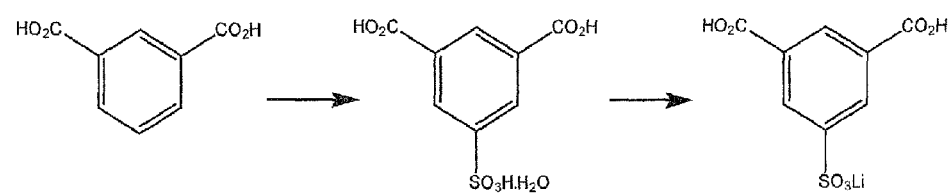

USE OF AN ACETIC ACID WASH TO PREPARE LOW-SULFATE 5-SULFOISOPHTHALIC ACID, MONO-LITHIUM SALT

This is the United States National Stage of Patent Cooperation Treaty Application No. PCT/US11/030,252 filed Mar. 29, 2011, which claims priority to Patent Cooperation Treaty Application No. PCT/US10/053,186 filed Oct. 19, 2010, the disclosures of which are incorporated herein by reference in their entireties.

CROSS REFERENCE TO RELATED APPLICATION

This application claims priority from commonly assigned PCT/US2010/053186 filed on 19 Oct. 2010.

BACKGROUND OF THE INVENTION

The present invention pertains to the field of polymer chemistry and specialty chemicals. More specifically, the present invention pertains to the field of polymer fibers and the specialized chemicals associated with developing dyed polymer fibers. In particular, this invention relates to the production of salt derivatives of isophthalic acid, specifically the production of an alkali metal salt derivative, such as a mono-lithium salt of 5-sulfoisophthalic acid, for use in the production of dyed nylon fibers among other polymer fibers.

Although derivatives of 5-sulfoisophthalic acid are used in several polymer processes this discussion will focus on nylon to aid in the understanding of the invention. The narrative and examples presented herein are for purposes of explanation and not of limitation.

Many types of nylons exist and are usually differentiated based on the components used to make them. Generally speaking, nylons are made by reacting equal parts of a diamine with a dicarboxylic acid. The particular diamine and acid used in the reaction gives the nylon its name. For example, "nylon 6-6" is a term used to identify nylon made by reacting hexamethylene diamine and adipic acid. Both components donate 6 carbons to the polymer chain thus the nylon is designated "6-6".

Nylon fibers, especially those used for carpet fiber, are also classified as to type, depending on the fiber's receptivity to acid dyes and basic or cationic dyes. Cationic dyeable nylon fiber generally exhibit inherent stain resistant properties as compared to other nylon types but traditionally suffered from poorer lightfastness, especially in light shades. This resulted in the under-utilization of cationic dyeable nylon as a carpet fiber.

As expected, considerable time, energy, and resources were devoted to finding new and improved methods to enhance the dye absorbing characteristics of cationic dyeable nylon. Over the years, several methods were developed in which very specialized chemicals were added to the fiber production process to impart improved cationic dye-ability to the polymer. One such specialized chemical is the lithium salt of 5-sulfoisophthalic acid, commonly known as LiSIPA.

The currently utilized processes for the production and purification of LiSIPA have numerous disadvantages, including a low product yield, colored product, and high manufacturing costs. Further, the resultant LiSIPA from known processes typically has a high sulfate level (i.e., above 500 ppm). More typically the sulfate levels in LiSIPA from known processes ranges from 1000 to 3000 ppm.

A problem inherent to the production of high sulfate LiSIPA is that the sulfate can precipitate in the fiber production process. Sulfate precipitation can lead to high levels of nylon filament breakage and lost production. It is believed that known LiSIPA products undergo additional treatment to reduce sulfate levels. However, such treatment increases production costs.

Another problem inherent to the high sulfate LiSIPA's produced by current methods is that there are limited means of removing the sulfate. For example, some of the sulfate can be removed by washing the LiSIPA with water or re-crystallizing the LiSIPA in water. Unfortunately, LiSIPA is soluble in water. Thus, using water for sulfate removal results in lost product.

Due to these and other problems in the prior art, some of which are disclosed herein, there is a need for a method of producing a LiSIPA product having inherently low sulfate content. In other words, there is a need for a method of producing LiSIPA that results in a LiSIPA product that has low levels of sulfate without any further treatment beyond simple collection and washing. The method should be suitable for commercialization using equipment currently employed in most LiSIPA manufacturing processes.

BRIEF SUMMARY OF THE INVENTION

In one aspect, the claimed invention is a process for the preparation of a low sulfate, lithium salt of 5-sulfoisophthalic acid. The process may begin with the formation of a solution of 5-sulfoisophthalic acid (HSIPA). The solution of HSIPA is drowned into a solution containing a lithium cation producing compound and water to form a reaction mixture. The reaction mixture is then maintained under conditions sufficient to form a lithium salt of 5-sulfoisophthalic acid. The lithium salt of 5-sulfoisophthalic acid is then isolated from the reaction mixture and washed with acetic acid.

The lithium salt of 5-sulfoisophthalic acid that is the product of this process contains very low sulfate (less than 500 ppm) as a non-purified composition of matter. In other words, the product need not be subjected to additional sulfate removing steps to achieve sulfate levels below 500 ppm.

BRIEF DESCRIPTION OF THE DRAWINGS

FIG. 1 is a schematic of an exemplary reaction incorporated in the process according to the invention.

DETAILED DESCRIPTION

As used herein, the terms "lithium salt of 5-sulfoisophthalic acid", "LiSIPA", and "LiSIPA product" encompass both the hydrated and anhydrous forms of the salt; the difference being the degree of drying of the final product.

As used herein, "low sulfate" means a LiSIPA composition containing less than 500 ppm sulfate ($SO_4^{2-}$), as compared to the typical process which results in a LiSIPA composition having sulfate levels in excess of 500 ppm, and more typically in the range of 1000 to 3000 ppm. Furthermore, the low sulfate product of the present invention is the non-purified, direct reaction product of the process.

As used herein, the term "non-purified" means that the reaction product that leaves the reaction vessel is not subjected to any further substantive processing or purification steps (other than filtering and washing) to achieve sulfate levels at or below 500 ppm. For example, some known processes currently use a "re-crystallization-in-water" step to reduce sulfate levels in the resulting LiSIPA product. The re-crystallization-in-water step is a difficult purification step that reduces overall yields due to the high solubility of LiSIPA in water. The process according to the invention avoids the costly "re-crystallization-in-water" and other post-manufacture purification steps.

The term "drowning" as used herein means the addition of one liquid component to another liquid component. In other words, the term means pouring a solution or intermediate slurry into a second liquid.

The phrase "consisting essentially of a lithium cation producing compound and water" is used in the context of describing a solution comprising a lithium cation producing compound and water and is free of any acetic acid. Other substances may be present to the extent they do not disrupt the reactions necessary to form a lithium salt of 5-sulfoisophthalic acid.

The method according to the invention in its simplified form comprises the steps of forming a solution containing 5-sulfoisophthalic acid (HSIPA) followed by drowning the HSIPA into an aqueous solution comprising a lithium cation producing compound to form a reaction mixture. The reaction mixture is then heated (if necessary) at a sufficient temperature for a sufficient period of time to produce a lithium salt of 5-sulfoisophthalic acid (LiSIPA), preferably a mono-lithium salt of 5-sulfoisophthalic acid. The LiSIPA is then isolated (e.g., filtered) and washed with acetic acid. The washed LiSIPA is then dried and packaged.

Those skilled in the art recognize that the steps outlined above for making LiSIPA can vary considerably in individual industrial processes. The following paragraphs set forth a possible embodiment of invention. This exemplary embodiment is provided to aid in the understanding of the invention and should not be interpreted as limiting the scope of the invention. Although the invention pertains to the manufacture of LiSIPA, the overall industrial process arguably begins with the production of 5-sulfoisophthalic acid (HSIPA) and this is where the discussion of this exemplary embodiment begins.

Turning now to FIG. 1, isophthalic acid is sulfonated to form HSIPA. There are several known methods for sulfonating isophthalic acid such as combining it with oleum or pure $SO_3$. Any of these known methods of producing HSIPA are acceptable in the practice of the invention. In this exemplary embodiment isophthalic acid is sulfonated by reacting it with oleum (aka "fuming sulfuric acid") under temperature and time conditions sufficient to form a crude solution of HSIPA in sulfuric acid. In a preferred embodiment the oleum is in solution at a concentration between about 20% and 60% and the sulfonation mixture is heated to a temperature between about 150° C. to about 230° C. for a time sufficient to form HSIPA.

The crude sulfonation solution of HSIPA is then drowned into an aqueous solution containing a lithium cation-producing compound to form a reaction mixture. In preferred embodiments the solution consists essentially of a lithium cation-producing compound and water. Other substances may be present to the extent they do not disrupt the reactions necessary to form a lithium salt of 5-sulfioisophthalic acid. Furthermore, the solution should be free of acetic acid. Other work conducted by the common assignee of this invention and discussed in co-pending PCT Application PCT/US2010/53186 relates to a process that utilizes a reaction mixture in which acetic acid is in excess. The current process removes acetic acid from the reaction mixture and is anticipated to be more cost effective in certain commercial applications (particularly those which lack the capability of recycling large amounts of acetic acid).

The lithium cation-producing compound may be any of several organic and inorganic compounds capable of producing lithium cations in an aqueous solution. Representative compounds include but are not limited to lithium hydroxide monohydrate, anhydrous lithium hydroxide, organic lithium salts such as lithium acetate, and inorganic lithium salts such as lithium carbonate, and lithium bicarbonate. In preferred embodiments the lithium cation-producing compound is lithium hydroxide monohydrate. The mole ratio of Li to HSIPA is ideally 1 to 1 but can be varied between 0.95 to 1 up to 1.05 to 1 or higher, with the cost of the lithium being the primary limiting factor. Preferably the lithium cation-producing compound is equal to or in slight excess as compared to the molar amount of HSIPA.

The reaction mixture is then maintained at reaction conditions sufficient to form a lithium salt of HSIPA (i.e., LiSIPA). Additional heating of the reaction mixture resulting from drowning step may not be necessary due to the temperature of the sulfonation mixture that is drowned into the aqueous solution containing the lithium cation. In most commercial applications of the invention it is anticipated that applying some heat to the reaction mixture will be necessary to achieve solution of the components. The temperature necessary to achieve solution will depend on the concentration of the various components of the reaction mixture. However, it is anticipated that in most commercial applications heating to reflux should be sufficient for all components to go into solution. The reflux temperature of the particular reaction mixture at atmospheric pressure should be the upper limit of the temperature necessary to achieve solution.

The drowning step (and any accompanying heating) to form the reaction mixture may occur very quickly (e.g., in minutes) or over an extended period of time (e.g., hours). The exact time utilized in any particular commercial practice of the invention will be governed in part by the available equipment but times between about 5 minutes and 2 hours are anticipated to be appropriate for most commercial applications. It is recommended that the drowning step be conducted over several minutes for safety, for gradual pH adjustment, and for thorough mixing of the HSIPA with the lithium cation to form LiSIPA.

The reaction mixture containing LiSIPA is then cooled to a temperature sufficient to initiate crystallization of LiSIPA. Typically this temperature is between 0° C. and 110° C. In most instances crystallization will occur between 60° C. and 100° C. In a preferred embodiment the reaction mixture is cooled during the crystallization step until it reaches about 25° C. The manner of cooling is not critical to the practice of the invention and those skilled in the art are capable of selecting the method most appropriate for their process (e.g., refrigeration). The crystallization step results in a crude LiSIPA that can be separated from the filtrate using any common filtration method, including but not limited to nutsches, centrufuges, autofilter dryers, etc., to form a crude LiSIPA cake.

After separation of the crude LiSIPA cake from the reaction mixture filtrate the LiSIPA is washed with acetic acid. The acetic acid used for the wash is preferably glacial acetic acid but solutions of acetic acid and water may also be used. However, if solutions of acetic acid and water are used the amount of water should be minimized because LiSIPA is soluble in water and washing with water can result in loss of product. A variation of this process, discussed below, that utilizes recycle of filtrate and wash streams can reduce product losses resulting from product solubility in water.

The acetic acid wash is applied by the method common to the filtration device (e.g., the wash is applied by pumping acetic acid into a nutsche filter). A quantity of acetic acid used is that which is sufficient to be drawn through the LiSIPA cake and displace/remove any remaining filtrate. The wash quantity can be varied from 15% of the weight of the LiSIPA cake to greater than 2 times the weight of the LiSIPA cake. Cost and the ability to recover the acetic acid are the primary constraints limiting the quantity of acetic acid wash used. The temperature of the acetic acid wash typically varies between about 18° C. and 60° C. but can be higher.

After the LiSIPA product is washed it is dried using any appropriate method known to those skilled in the art. The product can be isolated as an anhydrous solid or as a hydrate depending on the drying conditions (e.g., temperature, time and vacuum).

One of the benefits of the acetic acid wash process is that it does not form a solvate with the LiSIPA. This is a very surprising discovery considering how acetic acid interacts with a similar compound that is commonly used as an additive/component in polymer processes: the sodium salt of 5-sulfoisophthalic acid (NaSIPA). When acetic acid is used as a wash in the production of NaSIPA it forms a solvate with NaSIPA. The acetic acid that is carried along with the NaSIPA as a solvate can be very detrimental to polymer end-process (e.g, acetic acid can terminate polymerization). Furthermore, this NaSIPA/acetic acid solvate is very stable. Removal of the acetic acid from the NaSIPA typically requires temperatures in the range of 180° C. under vacuum. Temperatures this high usually result in discolored NaSIPA that is not suitable for use. Given that acetic acid causes so many problems with NaSIPA, it was assumed that acetic acid would cause similar problems with LiSIPA.

Accordingly, the discovery that acetic acid is an excellent wash for removing residual sulfate from LiSIPA was completely unexpected. Data collected to date supports the conclusion that acetic acid does not form a solvate with LiSIPA. Furthermore, it was surprisingly discovered that during drying steps under the application of heat and a vacuum, the acetic acid boils off the LiSIPA product prior to the water even though the boiling point of acetic acid is higher than that of water. This allows easy removal of acetic acid while still maintaining a LiSIPA hydrate if the hydrate is the desired end product.

Another benefit of using acetic acid as a wash in a LiSIPA process is that it results in a LiSIPA product with less color as compared to other processes that utilize ketones (e.g., acetone, MEK, etc.) as a wash. Washing with ketones allows for the formation of di- and polymeric ketone color bodies. Accordingly, ketone washes are typically followed by a second wash with hexane to remove the ketone, which further increases costs.

As mentioned previously, perhaps the primary benefit seen in the use of acetic acid as a wash is that it substantially reduces the quantity of residual sulfate in the final product. Using the method according to the invention it is possible to achieve product containing less than 500 ppm sulfate immediately after the wash step—no further purification or sulfate reduction steps are needed. In other words, the method according to the invention results in a non-purified reaction product composition of matter consisting essentially of a lithium salt of 5-sulfoisophthalic acid having less than 500 ppm sulfate. As noted previously, until now such a reaction product composition of matter has not been known. Furthermore, such low-sulfate LiSIPA is highly desired by the industry given the problems associated with having sulfate in the polymer end products and the expense of removing sulfate from LiSIPA made by traditional methods.

A variation to the process according to the invention has shown the ability to achieve a reaction product having less than 100 ppm sulfate. This variation incorporates the recycle of filtrates pulled from the reaction mixture during the filtration step.

As noted previously, LiSIPA is soluble to some extent in water. Accordingly, there is some loss of product via the filtrate in the filtering step. Furthermore, and as noted previously, some known processes for making LiSIPA utilize a wasteful "re-crystallization in water" step to purify isolated LiSIPA and remove sulfates. The question was then posed whether it would be possible to incorporate the solubility characteristics of LiSIPA that underlie the expensive "re-crystallization step" to make a traditional batch operation more efficient. In other words, would it be possible to use the hitherto bothersome solubility of LiSIPA in water to increase yields and reduce sulfate content even further. Additional experimentation showed that by recovering and reusing the filtrate from the reaction mixture one can recover lost product, which increases yields and reduces costs, while at the same time reducing sulfate content of the final product.

In very broad terms, this variation of the process according to the invention comprises the steps of combining previously isolated 5-sulfoisophthalic acid (HSIPA) with a solution comprising a lithium cation producing compound as described previously to form a first reaction mixture. The first reaction mixture is maintained under conditions sufficient to form a lithium salt of 5-sulfoisophthalic acid. The salt is then crystallized as discussed previously and filtered to form a product cake comprising a lithium salt of 5-sulfoisophthalic acid. The filtrate is collected. The product cake is washed with acetic acid and the wash is also collected.

The collected filtrate is then recycled to form a second reaction mixture comprising the collected filtrate, additional isolated HSIPA, and additional lithium cation-producing compound. The molar ratios of lithium to HSIPA for the second and subsequent batches are preferably the same as with the first batch (e.g., ideally 1 to 1 but can be varied between 0.95 to 1 up to 1.05 to 1 or higher). This second batch is reacted in the same way as the first and the cycle is repeated to form additional reaction mixtures. The process can continue for a series of 3-5 or even more batches.

Looking now at this variation in more detail, the process starts with isolated HSIPA, which is commercially available from a number of suppliers. The HSIPA utilized in the development of this variation was isolated as a chemical intermediate after sulfonation of isophthalic acid and drowning into water as is typical in commercial HSIPA processes. The resulting drowning solution was cooled to crystallize HSIPA, which was filtered and washed with acetic acid and dried in a vacuum oven.

The resulting solid HSIPA was reacted with lithium hydroxide (e.g., $LiOH.H_2O$) in a water solvent system to generate LiSIPA in a manner similar to that discussed above (e.g., at a Li to HSIPA mole ratio of 0.95:1 to 1.05:1 or higher). The resulting LiSIPA is isolated and filtered as before except the filtrate is collected and recycled for use in a subsequent batch with a purge rate of between about 5% to 7%. The purge rate aids in removal of trace amounts of sulfate that enter the system with the HSIPA.

The filtered LiSIPA is then washed with acetic acid as before except that the acetic acid wash is also collected and saved for an end of the run recovery of LiSIPA.

At the end of the desired series of batches the terminal recovered/recycled filtrate from the terminal reaction mixture and acetic acid washes are combined and concentrated via distillation. LiSIPA is recovered via crystallization and washed with acetic acid as before. Theoretically, the filtrate could be recycled indefinitely, however in practice it has been shown that four to five batches appear to be optimal to maintain the necessary product quality. Those skilled in the art will recognize that the optimal number of recycle batches will vary depending upon the individual characteristics of any given commercial production process.

Laboratory runs of this process variation that incorporates filtrate and acetic acid wash recovery resulted in a non-purified reaction product composition of matter consisting essentially of a lithium salt of 5-sulfioisophthalic acid having less than 100 ppm sulfate. In addition, yields increased due to recovery of LiSIPA that might have otherwise been lost in the filtrate. Using the recycle variation, the overall estimated yield from isophthalic acid to dry LiSIPA is about 73% and other lab data indicates that the yield from HSIPA to LiSIPA should average around 88% or greater during full scale production.

In view of the LiSIPA product that is obtained from the above processes, the claimed invention also encompasses a lithium salt of 5-sulfoisophthalic acid (e.g., a mono-lithium salt) that contains less than 500 ppm sulfate, more preferably less than 100 ppm sulfate.

It should be noted that the claimed processes for the production of LiSIPA utilizing an acetic acid wash are robust and can be varied in a number of different ways without impacting the resultant product quality. As the alternate embodiments of the disclosed process suggest, the process disclosed herein can be readily and easily modified. In fact, it should be noted that it is contemplated that the disclosed process can be modified in any manner known to those of skill in the art that is outside of the disclosed modifications and range changes.

Example 1

The following example begins with the sulfonation of isophthalic acid to form HSIPA as discussed in the detailed description. However, HSIPA is a commercially available product therefore the practice of the invention could start with HSIPA as well.

Isophthalic acid is added to excess $SO_3$ (as 30% oleum) to form a sulfonation solution. The sulfonation solution is heated to 195° C. to 210° C. and held for about 6 hours to form HSIPA.

The sulfonation solution is cooled and drowned into a solution of water and lithium hydroxide monohydrate that is between 0° C. and 110° C. to form a solution of 5-sulfoisophthalic acid mono-lithium salt. The product is crystallized while cooling the solution to 0° C. to 25° C., thus forming a slurry of 5-sulfoisophthalic acid mono-lithium salt.

One quart slurry samples of 5-sulfoisophthalic acid mono-lithium salt from a standard plant production batch (as described above) were collected after a standard crystallization step (e.g., cooling to crystallization temperature). A 1000 ml sintered glass funnel was set up. A full quart of LiSIPA slurry was introduced to the funnel under a vacuum draw. The majority of the filtrate was removed after about 85 seconds to leave a crude LiSIPA cake. Glacial acetic acid at about 25° C. was added to the cake under a vacuum draw. The quantity of acetic acid can vary between about 15% and 200% of the estimated product dry weight. The vacuum was applied for about 120 seconds.

The washed cake was then dried in an oven at 90° C. to about 100° C. overnight to generate a LiSIPA hydrate. Increasing the heat to 100° C. to about 130° C. will generate the anhydrous salt. Application of a vacuum during the drying step is optional but preferred.

A sample of the dried product assayed as follows (results are typical of other samples):

| Sample No. 1 | |
| --- | --- |
| Product wet weight (grams) | 238.5 g |
| Product dry weight (grams) | 209.9 g |
| Solids % | 88.1% |
| Total Acidity as LiSIPA | 96.4% |
| Neutralization equivalent | 130 |
| Water, % | 3.6 |
| Sulfate, ppm as $SO_4^{2-}$ (Ion Chromatography) | 459 ppm |
| Acetate, ppm as $OAc^{-1}$ (Ion Chromatography) | 234 ppm |

Example 2

The following example begins with isolated HSIPA and illustrates the process according to the invention where filtrate and acetic acid washes are recovered and recycled. The HSIPA utilized in the development of this variation was isolated as a chemical intermediate after sulfonation of isophthalic acid and drowning into water as is typical in commercial HSIPA processes. The resulting drowning solution was cooled to crystallize HSIPA, which was filtered and washed with acetic acid and dried in a vacuum oven.

For the first batch in the series a 1000 ml round bottom flask was set up. Eighty (80) g of fresh deionized water was added to the flask. It should be noted that for each batch in the series 80 g total of water was used. Therefore, for the second and subsequent series in which the filtrate is recycled a small amount of fresh deionized water will be required due to process losses and the 5-7% purge. The total grams of water used in the second and subsequent batches is generically calculated as follows:

total g of water(80 g)=[g of water in filtrate]+[g water in HSIPA]+[g of fresh water]

To the 80 g of fresh water was added 32.75 g of lithium hydroxide ($LiOH.H_2O$). The water/LiOH mixture was heated to between 25° C. and 45° C. at which time 200 g of HSIPA was added to the flask. This provides a Li:HSIPA mole ratio of about 0.96:1. The reaction mixture was heated to reflux (about 113° C.) and held for 30 minutes.

The reaction mixture was then cooled to about 55° C. and held at that temperature for about 30 minutes after which time it was rapidly cooled in an ice bath to about 15° C. The LiSIPA product crystallized and was isolated by vacuum filtration through a LabGlass® sintered glass filter. The filtrate was collected for recycle.

The resulting LiSIPA cake was washed with 35 g of ambient temperature acetic acid. The wash was also collected.

The majority of the filtrate from the prior batch plus the makeup water needed to get to a total of 80 g of water is added to the round bottom flask, followed by the addition of 16.37 g of lithium hydroxide monohydrate and 100 g of HSIPA to form a reaction mixture. This lesser quantity of lithium hydroxide for the second and subsequent batches is to allow for a normal weight of product for the first batch (no recycled filtrate) as compared to the subsequent batches with filtrate recycle. Overall, the amount of lithium hydroxide ($LiOH.H_2O$) added to the second and subsequent batches should be that quantity necessary to keep the molar ratio of $LiOH.H_2O$:HSIPA around 0.95:1 to 1.05:1 or higher.

The reaction mixture is heated to reflux, cooled, and the resulting product filtered as with the first batch. The product is washed as before and the acetic acid is collected.

Additional recycle batches may be run. Current data indicates that 3-5 recycle batches are optimal for maximizing the recycle capabilities while maintaining product quality.

After the final batch is completed, the collected filtrate and acetic acid washes are worked up for product recovery.

Again, a 1000 ml round bottom flask was set up to receive (1) the filtrate from the terminal batch, (2) all of the acetic acid washes, and (3) any filtrate heels that may have been collected. This mixture is heated to reflux to distill off low boilers until the mixture is about 70 to 75% of its original weight.

The distilled recycle mixture is then cooled to about 55° C., held for about 30 minutes, then rapidly cooled to 15° C. The resulting crystallized product is then filtered under vacuum through a LabGlass® sintered glass filter. After 5 minutes of vacuum filtration the resulting cake is washed with an excess of acetic acid. Thirty five (35) g of acetic acid was used in the trial processes. The washed cake was then dried overnight under vacuum at about 115° C.

Two series of multiple batch runs were conducted. The first series used 5 batches and resulted in LiSIPA product having less than 100 ppm sulfate with an overall process yield from HSIPA to LiSIPA of about 86.6%. The second series used 4 batches and resulted in LiSIPA product having less than 104 ppm sulfate with an overall process yield of about 83.6%.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A process for the preparation of a low sulfate, lithium salt of 5-sulfoisophthalic acid, the process comprising the steps of
   drowning a solution of 5-sulfoisophthalic acid into a solution consisting essentially of a lithium cation producing compound and water to form a reaction mixture;
   maintaining the reaction mixture under conditions sufficient to form a lithium salt of 5-sulfoisophthalic acid;
   isolating said lithium salt of 5-sulfoisophthalic acid from the reaction mixture; and
   washing said isolated lithium salt of 5-sulfoisophthalic acid with acetic acid.

2. A process according to claim 1 further comprising the prior step of forming 5-sulfoisophthalic acid from isophthalic acid and oleum or sulfuric acid.

3. A process according to claim 1 wherein said lithium cation producing compound is selected from the group consisting of organic lithium salts, and inorganic lithium salts.

4. A process according to claim 1 wherein the lithium cation producing compound is lithium hydroxide monohydrate or anhydrous lithium hydroxide.

5. A process according to claim 3 where the organic lithium salt is lithium acetate and the inorganic lithium salt is selected from the group consisting of lithium carbonate and lithium bicarbonate.

6. A process according to claim 1 wherein the mole ratio of lithium cation to 5-sulfoisophthalic acid is at least 0.95:1.

7. A process according to claim 1 wherein the step of maintaining the reaction mixture comprises heating the reaction mixture to reflux for a time between about 5 minutes and 2 hours.

8. A process according to claim 1 wherein the step of isolating said lithium salt of 5-sulfoisophthalic acid from the reaction mixture comprises inducing crystallization of said lithium salt of 5-sulfoisophthalic acid.

9. A process according to claim 1 further comprising the step of drying the washed lithium salt of 5-sulfoisophthalic acid.

10. A process for the preparation of a low-sulfate, monolithium salt of 5-sulfoisophthalic acid, the method comprising the steps of:
    drowning a solution of 5-sulfoisophthalic acid into a solution comprising a lithium cation producing compound and water to form a reaction mixture;
    maintaining the reaction mixture under conditions sufficient to form a lithium salt of 5-sulfoisophthalic acid;
    filtering the lithium salt of 5-sulfoisophthalic acid to form a product cake;
    washing the product cake with acetic acid; and
    drying the washed cake containing the lithium salt of 5-sulfoisophthalic acid.

11. A process according to claim 10 wherein said lithium cation producing compound is selected from the group consisting of organic lithium salts, and inorganic lithium salts.

12. A process according to claim 11 wherein said lithium cation producing compound is lithium hydroxide monohydrate or anhydrous lithium hydroxide.

13. A process for the preparation of a low-sulfate, monolithium salt of 5-sulfoisophthalic acid, the method comprising the steps of:
    drowning a solution of 5-sulfoisophthalic acid into a solution comprising a lithium cation producing compound and water to form a reaction mixture which is free of acetic acid;
    maintaining the reaction mixture under conditions sufficient to form a lithium salt of 5-sulfoisophthalic acid;
    filtering the lithium salt to form a product cake; and
    washing the product cake with acetic acid.

14. A process according to claim 13 wherein said lithium cation producing compound is selected from the group consisting of lithium hydroxide monohydrate, anhydrous lithium hydroxide, organic lithium salts, and inorganic lithium salts.

15. A process for the preparation of a low-sulfate, monolithium salt of 5-sulfoisophthalic acid, the method comprising the steps of:
    combining isolated 5-sulfoisophthalic acid with a solution comprising a lithium cation producing compound and water to form a first reaction mixture;
    maintaining the first reaction mixture under conditions sufficient to form a lithium salt of 5-sulfoisophthalic acid;
    filtering the first reaction mixture to form a product cake comprising a lithium salt of 5-sulfoisophthalic acid and a collected filtrate; washing the product with acetic acid and collecting at least a portion of the acetic acid wash; and
    recycling the collected filtrate to form a second reaction mixture comprising the collected filtrate and isolated 5-sulfoisophthalic acid.

16. A process according to claim 15 wherein additional reaction mixtures are formed from recycled filtrates.

* * * * *